(12) United States Patent
Lu

(10) Patent No.: US 6,884,236 B1
(45) Date of Patent: Apr. 26, 2005

(54) DISPOSAL STERILE SYRINGE WITH RETRACTABLE TAPER

(76) Inventor: Chun-Hui Lu, No. 20, Wufu St., Jhongli City, Taoyuan County (TW)

( * ) Notice: Subject to any disclaimer, the term of this patent is extended or adjusted under 35 U.S.C. 154(b) by 0 days.

(21) Appl. No.: 10/825,105

(22) Filed: Apr. 16, 2004

(51) Int. Cl.⁷ .................................................. A61M 5/00
(52) U.S. Cl. ....................................................... 604/110
(58) Field of Search ................................ 604/110, 181, 604/187, 195, 218, 221, 222, 239, 243, 272, 228

(56) References Cited

U.S. PATENT DOCUMENTS

| | | | | |
|---|---|---|---|---|
| 4,790,822 A | * | 12/1988 | Haining | 604/110 |
| 4,915,692 A | * | 4/1990 | Verlier | 604/110 |
| 4,950,241 A | * | 8/1990 | Ranford | 604/110 |
| 5,122,124 A | * | 6/1992 | Novacek et al. | 604/195 |
| 5,380,285 A | * | 1/1995 | Jenson | 604/110 |
| 5,415,638 A | * | 5/1995 | Novacek et al. | 604/110 |
| 5,634,903 A | * | 6/1997 | Kurose et al. | 604/110 |
| 2003/0060775 A1 | * | 3/2003 | Shyu | 604/197 |

* cited by examiner

Primary Examiner—Sharon Kennedy
(74) Attorney, Agent, or Firm—Troxell Law Office, PLLC

(57) ABSTRACT

A disposable sterile syringe with retractable taper; wherein, its lower needle lock inserted into injection way via the through hole in the lower needle lock, the needle lock being place and secured in the barrel by having the locking nipple on the upper edge of the lower needle lock and the locking nipple on the lower needle lock respectively engaged to the flange of the lower needle lock and the scalene cone on the upper needle lock; the taper being secured to the upper needle lock; and the plunger being inserted into the barrel.

8 Claims, 4 Drawing Sheets

DISPOSAL STERILE SYRINGE WITH RETRACTABLE TAPER

BACKGROUND OF THE INVENTION (a) Field of the Invention

The present invention is related to a disposal sterile syringe with retractable taper, and more particularly, to one that has a nose cone in front of the plunger locked in the through hole of the needle lock to retract the needle lock and the taper for receiving the needle in the barrel.

(b) Description of the Prior Art

Whereas the conventional syringe allows repeated use for injection after sterilization, any insufficient sterilization may cause infection. Therefore, a disposable sterile syringe is available, however, there is no protection provided for the taper of the disposable sterile syringe. Accordingly, the taper disposed may puncture the person handling the disposal to result in another type of infection and injury.

SUMMARY OF THE INVENTION

The primary purpose of the present invention is to provide a disposal sterile syringe that retracts the needle lock and the taper into the barrel to avoid repeated use of the syringe and protect it from puncturing anyone may be required to handle the disposal of the syringe. To achieve the purpose, the lower needle lock is inserted into the injection way and the needle lock is then inserted into the barrel. A locking nipple on the upper edge of the lower needle lock and that on the lower needle lock are respectively engaged the flange of the lower needle lock and the scalene cone of the upper needle lock before having the needle to be disposed in the upper needle lock. Finally, the plunger is placed into the barrel to complete the assembly of the present invention. After the injection, push the plunger all the way down the barrel, and the locking nose cone at the front end of the plunger is pushed into the through hole in the lower needle lock for the locking nose cone to be interlocked with the lower needle lock. Then the plunger is pulled back to retract the needle lock and the needle into the barrel at the same time to avoid repeated use of the syringe and to prevent any accidental puncture of the needle from causing any injury or infection.

Particularly, a cut is reserved on one side of the plunger at where close to the locking ring holder. The cut is exactly located at the flange of the barrel so that the portion of the plunger exposed from the cut can be easily broken up to make sure that the needle and the needle lock are contained in the barrel to further ensure of the safe and convenient use of the disposal sterile syringe.

DETAILED DESCRIPTION OF THE PREFERRED EMBODIMENTS

Figure 1:
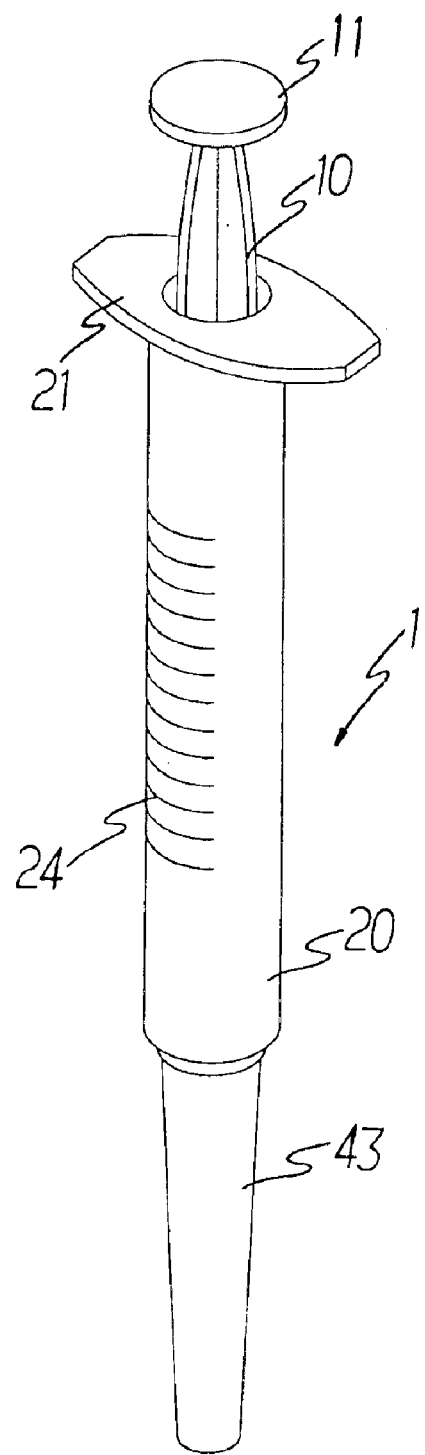
FIG. 1 is a perspective view of the present invention.
Figure 2:
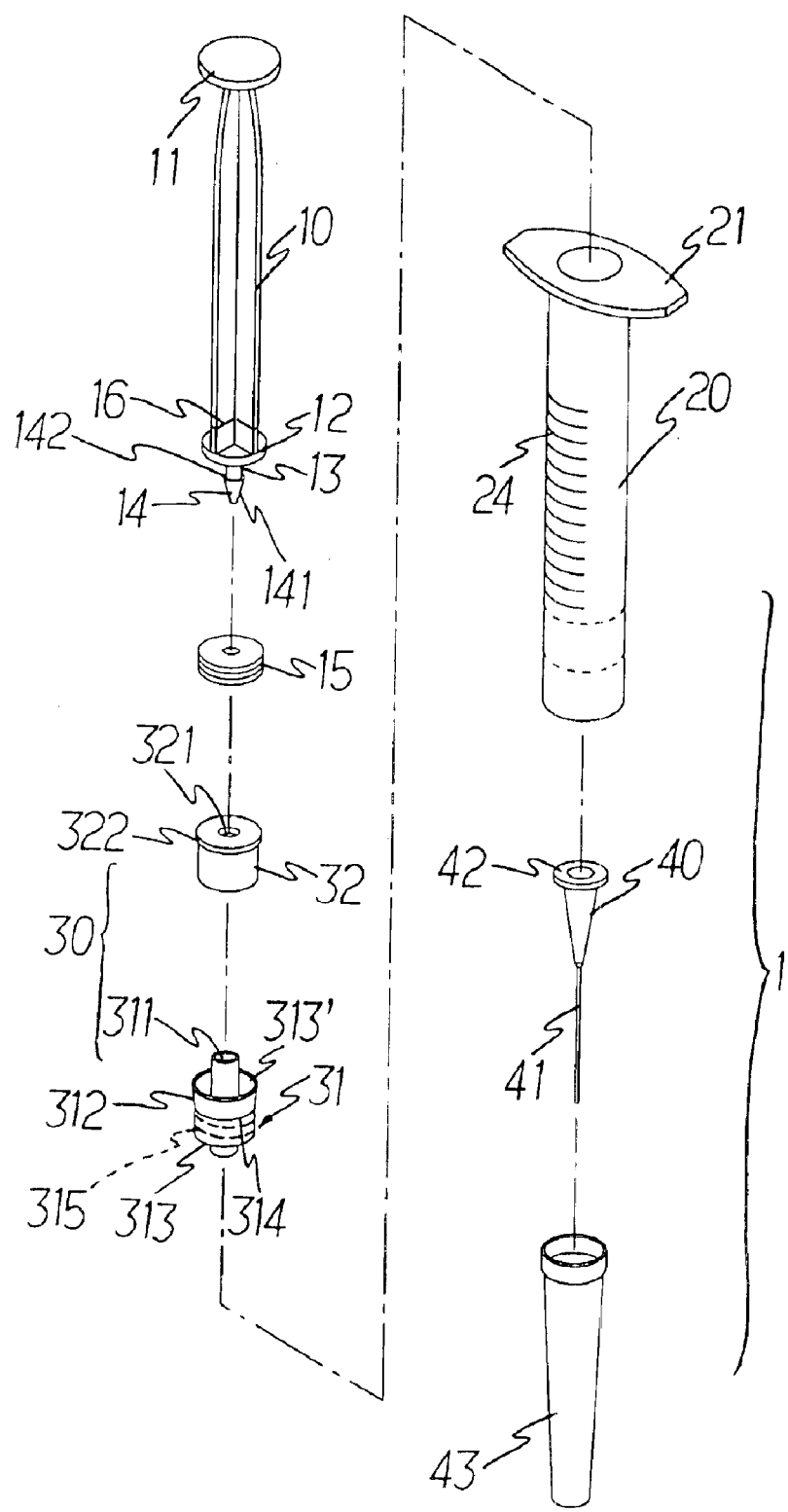
FIG. 2 is an exploded view of the present invention.
Figure 3:
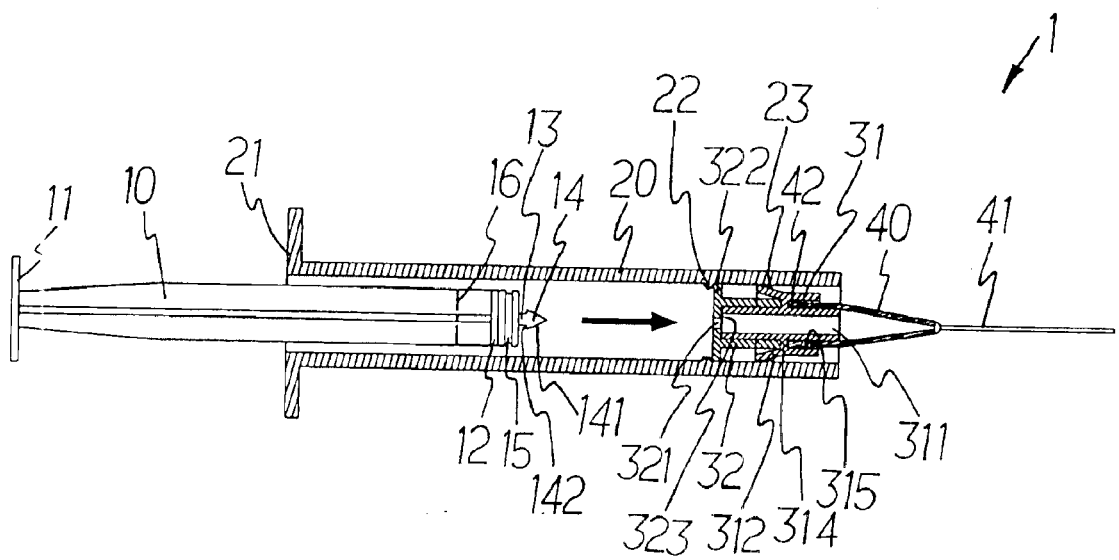
FIG. 3 is a schematic view of the present invention when assembled.

Referring to FIGS. 1 through 3, a disposal sterile syringe 1 of the present invention includes of a plunger 10, a barrel 20, a needle lock 30, and a taper 40. Wherein, the plunger 10 has at its rear end provided with a flange 11; its front end, a plunger retainer 12; the plunger retainer 12 is comprised of a locking ring holder 13 and a locking nose cone 14; a ring plug 15 is provided on the locking ring holder 13; and the locking nose cone 14 is made in an arrow shape formed on one side a guiding edge 141 and a hooking member 142.

The barrel 20 has at its rear end disposed with a flange 21, and a range of scale 24 on the body of the barrel 20; and a locking nipple 22 on the upper edge of a lower needle lock 32 and another locking nipple 23 on the lower needle lock 32 are provided in sequence in the inner edge of the barrel 20 on the distal side from the flange 21.

The needle lock 30 is comprised of an upper needle lock 31 and the lower needle lock 32; wherein, an injection way 311 penetrates through the upper needle lock 31; a scalene cone 312 externally expanding toward the side of the lower needle lock 32 is provided on the upper needle lock 31 at where close to the side of the lower needle lock 32; a groove is provided surrounding the external circumference of the injection way 311 of the upper needle lock 31, and is divided into an upper groove 313 and a lower groove 313' by a partitioning plate 314; the upper groove is disposed with an internal thread 315 while the lower needle lock is comprised of a through hole 321 and a flange 322; and a retainer edge 323 is provided on one side of the inner wall of the through hole 321.

The taper 40 has its one end fixed with a needle 41 and another end disposed with a flange 42 with the taper 40 contained in the upper needle lock 31 of the needle lock 30.

Upon assembling, the lower needle lock 32 is inserted into the injection way 311 by the through hole 321; the needle lock 30 is then placed into the barrel 20; the needle lock 30 is secured in the barrel 20 by having the locking nipple 22 on the upper edge of the lower needle lock 32 and the locking nipple 23 on the lower needle lock 32 respectively engaged to the flange 322 of the lower needle lock 32 and the scalene cone 312 on the upper needle lock 31; the taper 40 is placed in the upper needle lock 31 by having the flange 42 of the taper 40 screwed into the upper groove 313; a cap 43 is provided to cover up the needle 41; and finally the plunger 10 is inserted into the barrel 20 to complete the assembly of the syringe 1.

Figure 4:
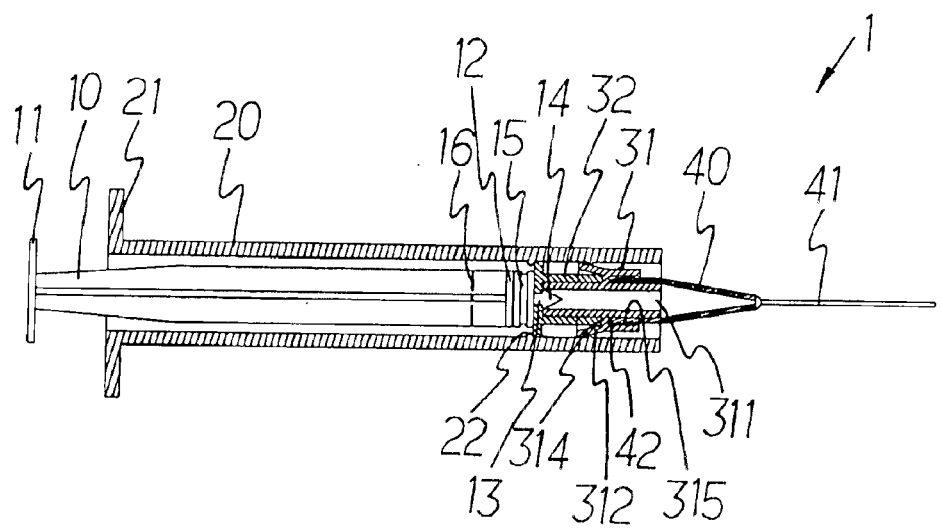
FIG. 4 is a schematic view showing the plunger and the needle lock of the present invention.
Figure 5:
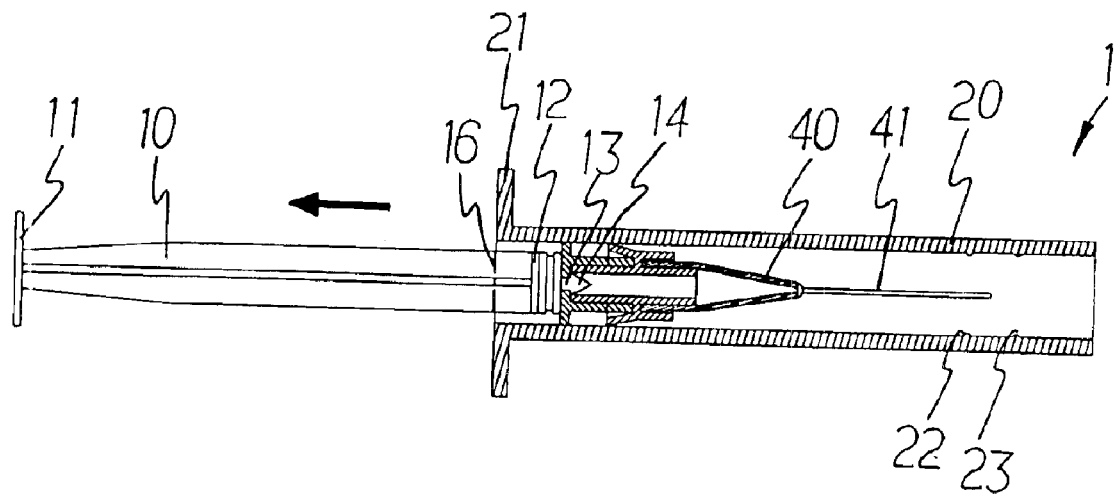
FIG. 5 is a schematic view showing that both of needle lock and the taper are retracted into the barrel by the plunger.

When used in injection, an injection liquid A in the barrel 20 is pushed forward by the plunger 10 to flow through the injection way 311 via the through hole 321 of the lower needle lock 32 through the needle 41 to punctuate the human skin. Upon completing the injection of the injection liquid A, the plunger 10 is further pushed all way down the barrel as illustrated in FIG. 4, so that the locking nose cone 14 at the front end of the plunger 10 is pushed into the through hole 321 of the lower needle lock 32 and is secured by having the hooking member 142 interlocked with the retainer edge 323 of the through hole 321; then the plunger 10 is pulled back for both of the needle lock 30 and the taper 40 to retract into the barrel as illustrated in FIG. 5 to prevent repeated use of the barrel and to prevent any accidental punctuation by the taper 40 to cause any injury of infection.

Figure 6:
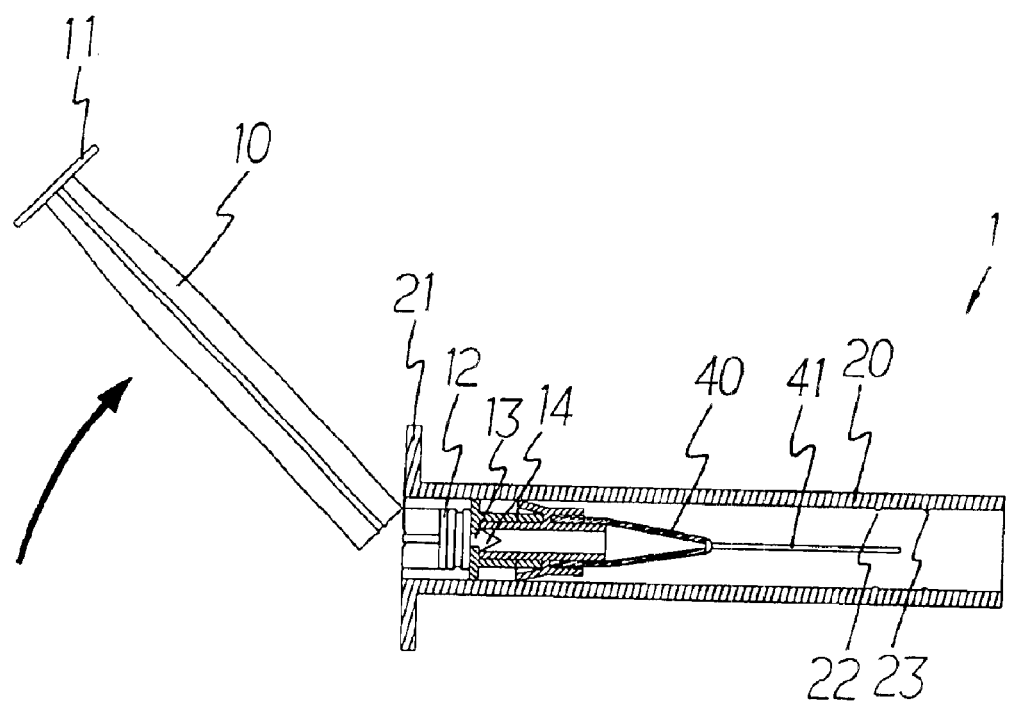
FIG. 6 is a schematic view showing that the plunger is broken up.

Furthermore, a cut 16 is reserved on one side of the plunger 10 at where close to the locking ring holder 13 so that when the plunger 10 is pulled back to its extreme, the cut 16 is exactly located at the flange 21 of the barrel 20 to break up the portion of the plunger 10 exposed above the cut 16 as illustrated in FIG. 6 to make sure that both of the taper 40 and the needle lock 30 are well stored in the barrel to further improve the safe and convenient use of the syringe 1.

The present invention by providing a locking nose cone at the front end of the plunger for it to be locked in the through hole of the needle lock so that both of the taper and the needle lock can be retracted into the barrel at the same time to facilitate the storage of the taper in the barrel provides a safe use of the disposal sterile syringe; therefore, this application for a utility patent is duly filed accordingly. However, it is to be noted that the preferred embodiment and the accompanying drawings described above are not to limit the present invention; therefore, any structure, device, and characteristics that are similar to or identical with that of the present invention shall be deemed as falling within the scope of the purpose and claims made by the present invention.

I claim:

1. A disposable sterile syringe with retractable taper includes a plunger, a barrel, a needle lock and a taper; wherein, the plunger having at its rear end disposed with a flange, a plunger locking holder comprised of a locking ring holder and a locking nose cone at its front end, and a ring plug provided surrounding the locking ring holder; the barrel having at its rear end provided with a flange, a range of scale on the body of the barrel, a locking nipple on the upper edge of a lower needle lock and another locking nipple on the lower needle lock being provided in sequence to the inner edge of the barrel on the distal side from the flange; the needle lock comprised of an upper needle lock and the lower needle lock, an injection way penetrating through the upper needle lock; a scalene cone externally expanding toward the side of the lower needle lock being disposed on the upper needle lock close to the side of the lower needle lock; a groove being provided surrounding the external circumference of the injection way of the upper needle lock and divided into an upper groove and a lower groove by a partitioning plate, the upper groove being disposed with an internal thread while the lower needle lock being comprised of a through hole and a flange, and a retainer edge being provided on one side of the inner wall of the through hole; and the taper, having its one end fixed with a needle and another end disposed with a flange with the taper contained in the upper needle lock of the needle lock is characterized by that: the lower needle lock being inserted into the injection way by the through hole, the needle lock then placed into the barrel, the needle lock secured in the barrel by having the locking nipple on the upper edge of the lower needle lock and the locking nipple on the lower needle lock respectively engaged to the flange of the lower needle lock and the scalene cone on the upper needle lock, the taper being placed in the upper needle lock by having the flange of the taper screwed into the upper groove, a cap being provided to cover up the needle, and the plunger being inserted into the barrel; upon completing the injection the plunger being pushed all way down the barrel, the locking nose cone at the front end of the plunger being pushed into the through hole of the lower needle lock and secured by having the hooking member interlocked with the retainer edge of the through hole, and the plunger being pulled back for both of the needle lock and the taper to retract into the barrel.

2. A disposable sterile syringe with retractable taper as claimed in claim 1, wherein, a cut is reserved on the plunger at where close to the locking ring holder at a location exactly falling on the flange of the barrel when the plunger is pulled back to its extreme; and the plunger exposed from the cut after the use of the syringe can be broken up.

3. A disposable sterile syringe with retractable taper as claimed in claim 1, wherein, a groove is provided surrounding the external circumference of the injection way in the upper needle lock and is divided into the upper groove and the lower groove with a partitioning plate.

4. A disposable sterile syringe with retractable taper as claimed in claim 1, wherein, the inner circumference of the upper groove is threaded to engage the flange of the taper.

5. A disposable sterile syringe with retractable taper as claimed in claim 1, wherein, the scalene cone on the upper needle lock external expanding towards the side of the lower needle lock.

6. A disposable sterile syringe with retractable taper as claimed in claim 1, wherein, the locking nose cone is made in an arrow shape having on its one side formed with a guiding edge and a hooking member for the locking nose cone to be interlocked with the retainer edge of the through hole with the hooking member.

7. A disposable sterile syringe with retractable taper as claimed in claim 1, wherein, the body of the barrel is provided with a range of scale.

8. A disposable sterile syringe with retractable taper as claimed in claim 1, wherein, a cap is provided to cover up the taper.

* * * * *